United States Patent [19]

Teves

[11] Patent Number: 5,348,000
[45] Date of Patent: Sep. 20, 1994

[54] APPARATUS AND METHOD FOR DISPENSING OXYGEN AND ANESTHESIA VIA INTERCHANGEABLE FACEMASK AND NASAL CATHETER

[76] Inventor: Leonides Y. Teves, 623 39th St. W., Bradenton, Fla. 34205

[21] Appl. No.: 93,425
[22] Filed: Jul. 19, 1993
[51] Int. Cl.$^5$ ............ A61M 15/08; A61M 11/00; A62B 7/00; A62B 18/02
[52] U.S. Cl. ............ 128/204.18; 128/205.25; 128/207.18; 128/912; 128/DIG. 26; 604/94
[58] Field of Search ............ 128/207.18, 911, 912, 128/DIG. 26, 201.24, 206.29, 206.25, 204.18; 604/94

[56] References Cited

U.S. PATENT DOCUMENTS

| | | | |
|---|---|---|---|
| 2,360,193 | 10/1944 | Boothby et al. | 128/206.29 |
| 2,625,155 | 1/1953 | Engelder | 128/206.24 |
| 3,515,135 | 6/1970 | Flower et al. | 128/205.25 |
| 4,263,908 | 4/1981 | Mizerak | 128/207.18 |
| 4,580,556 | 4/1986 | Kondur | 128/206.29 |
| 4,848,331 | 7/1989 | Northway-Meyer | 128/207.14 |
| 4,915,105 | 4/1990 | Lee | 128/207.18 |
| 4,936,298 | 6/1990 | Nishina et al. | 128/206.29 |
| 5,197,463 | 3/1993 | Jeshuran | 128/207.14 |
| 5,243,971 | 9/1993 | Sullivan et al. | 128/207.18 |

Primary Examiner—Kimberly L. Asher
Attorney, Agent, or Firm—Joseph C. Mason, Jr.; Ronald E. Smith

[57] ABSTRACT

The proximal end of a nasal oxygen catheter is modified so that it releasably engages a facemask coupler that is in fluid communication with an anesthesia machine. A facemask is also releasably engaged to the facemask coupler. The distal end of the catheter includes nasal prongs and oxygen only from the anesthesia machine is dispensed to the patient through the prongs when the proximal end of the catheter is engaged with the facemask coupler. Upon disengagement of the proximal end of the catheter from the coupler, the facemask may be applied to the nose and mouth of a patient without reconfiguring the anesthesia machine. The anesthesia or oxygen-dispensing capabilities of the anesthesia machine are not disabled by any configuration of parts so that the machine may be reconfigured from an oxygen-only mode to an oxygen-and-anesthesia mode in only a second or two.

2 Claims, 4 Drawing Sheets

APPARATUS AND METHOD FOR DISPENSING OXYGEN AND ANESTHESIA VIA INTERCHANGEABLE FACEMASK AND NASAL CATHETER

BACKGROUND OF THE INVENTION

1. Field of the Invention

This invention relates to improvements in equipment used in connection with anesthesia machines and methods for use of such improved equipment. More particularly, it relates to an apparatus and method that eliminates the need to disable the anesthesia-dispensing capability of an anesthesia machine when it is configured to dispense oxygen only to a patient.

2. Description of the Prior Art

Anesthesia machines are capable of dispensing both oxygen and anesthesia (usually nitrous oxide) to patients. They may also be used to deliver oxygen only, but for safety reasons they are not designed to deliver anesthesia only. Typically, they include a main outlet dedicated to supplying a mixture of anesthesia and oxygen to a patient; an elongate flexible supply tube extends from said main outlet to a facemask that is fitted over the patient's nose and mouth to deliver the anesthesia/oxygen mixture to the patient's lungs. An elongate flexible return tube extends from the facemask to the machine and returns exhaled carbon dioxide and other gases to the machine.

When the facemask is in position over the patient's nose and mouth, the machine can be set to deliver any mixture of nitrous oxide and oxygen to the facemask. Importantly, the nitrous oxide is entrained by the oxygen flow, i.e., if oxygen does not flow, the nitrous oxide cannot flow.

There are many operations, such as eye operations, that do not require general anesthesia. A local anesthetic is generally used in such situations, and the patient remains conscious throughout the surgical procedure. Due to the uncertainties inherent in any use of general anesthesia, the use of local anesthetics is usually preferable. Patients under local anesthesia are usually given oxygen from the anesthesia machine, but the facemask is not used in those situations, such as eye surgery, because it would physically interfere with the surgical procedures. In such situations, an elongate nasal oxygen catheter is employed; such a catheter has a proximal end in fluid communication with the machine and further has a pair of nasal prongs at its distal end that are fitted into the patient's nostrils. When a nasal catheter is used, oxygen from the machine is delivered to the patient and no appreciable obstruction to the surgical procedure is presented.

A major shortcoming of the known anesthesia machines is that their parts must be reconfigured when a patient is to receive oxygen only from the machine; such reconfiguration disables the anesthesia-dispensing capability of the machine and such disabling can have catastrophic consequences.

The reconfiguration procedure includes the steps of adding an elbow member to the machine and attaching the proximal end of an elongate nasal oxygen catheter to said elbow so that oxygen from the machine that would normally flow to the patient through the main supply tube and hence to the facemask is re-routed through the elbow into said nasal oxygen catheter. Significantly, since the flow of oxygen is diverted to the elbow and the catheter, no nitrous oxide can be delivered to the patient. Thus, whenever a patient is receiving oxygen through a nasal catheter, the anesthesia-dispensing capability of the anesthesia machine is nonfunctional.

If the patient becomes uncomfortable because the local anesthetic is inadequate, it takes several minutes (usually about three minutes) to reconfigure the anesthesia machine so that it can supply nitrous oxide to the patient. During the three minute reconfiguration, the patient may suffer pain, may complain loudly, and may even become belligerent. Some patients stand up on the operating table, some attempt to leave the operating room, and so on. Under these conditions, the anesthesiologist needs to put the patient under general anesthesia quickly.

Changing the anesthesia machine from an oxygen-only mode to its anesthesia and oxygen mode is time-consuming because the elbow member must be removed from the machine, the oxygen hose must be reattached to the machine, the prongs at the distal end of the catheter must be removed from the patient's nostrils, the machine must be set to deliver the right mixture of nitrous oxide and oxygen, and the facemask must be placed into position over the patient's nose and mouth.

The existing method for delivering oxygen only to a patient has an even worse side effect. When an operation is successfully concluded by a surgical team where the patient received oxygen only and a local anesthetic, the surgical team will frequently forget to reconfigure the machine back into its anesthesia/oxygen mode, i.e., they will leave the operating theater with the elbow still attached to the machine. Thus, when the next surgical team having a patient who needs to be placed under general anesthesia uses the machine, a crisis will erupt when the surgical team notices that the patient is exhibiting the symptoms of oxygen deprivation, even though the facemask is in place and the anesthesia machine appears to be functioning normally. In the course of a frantic search for the cause of the apparent malfunction of the anesthesia machine, a member of the team will eventually notice that the elbow member is hooked up and that all of the machine's oxygen is being pumped into the room, bypassing the machine and hence preventing the flow of anesthesia and oxygen to the facemask. The elbow will then be yanked out, the oxygen hose will be placed into its proper port, and the crisis will end happily if the problem was found and fixed quickly enough.

Thus, there is a need for improvements in the methods of use of anesthesia machines and related equipment and there is a need for improvements in the related equipment. The improved equipment would enable a physician to switch from oxygen only to anesthesia and oxygen quickly. Just as importantly, the improved machine would not require the disconnection of the oxygen supply and the concomitant disabling of the machine's ability to dispense anesthesia at any time. Thus, subsequent users of the machine would never need to reconfigure it in order to avoid problems.

However, at the time the present invention was made, it was not obvious to those of ordinary skill in this art how the known methods of use of anesthesia machines could be improved, and how the related equipment could be made better.

SUMMARY OF THE INVENTION

This invention is based upon the insight that the facemask which is ordinarily used for the delivery of an oxygen/anesthesia mixture to the nose and mouth of a patient may also be employed for delivering oxygen only to the proximal end of a nasal oxygen catheter and hence to the nasal prongs at the distal end thereof. A connector at the proximal end of a nasal oxygen catheter, which is normally configured and dimensioned for attachment to the elbow member that causes the oxygen to bypass the machine, is modified so that said proximal end is press fittingly engageable with said facemask instead of said elbow member.

Thus, with the proximal end of the nasal oxygen catheter press fit into the facemask, oxygen from the anesthesia machine is delivered to the patient through the nostril prongs at the distal end of the nasal oxygen catheter; the elbow member of the prior art, and the concomitant disabling of the machine's ability to dispense anesthesia, is not needed and does not occur, respectively. If the patient suddenly requires general anesthesia, the proximal end of the nasal oxygen catheter is pulled out of its press fit engagement with the facemask, the nostril prongs at the distal end of the catheter are removed from the patient's nostrils, and the facemask is placed over the patient's nose and mouth. Thus, the time between the need for general anesthesia and the delivery thereof is a very short time, i.e., a second or two. Perhaps even more importantly, the elbow for routing oxygen flow in bypassing relation to the machine is never employed. The ability of the machine to deliver anesthesia is never disabled and the machine is therefore always ready for use by the next surgical team.

Thus, it should be understood that a general object of the present invention is to provide improvements in methods for using anesthesia machines.

A more specific object is to provide a method for using an anesthesia machine where the oxygen flow thereof is never rerouted from its normal path of travel and the machine's ability to dispense nitrous oxide is never disabled.

Another very important object is to provide a new method for delivering oxygen only to a patient so that a changeover from oxygen only to a mixture of anesthesia and oxygen can be made in a second or so.

Another object is to provide a new method for delivering oxygen that cannot result in a subsequent surgical team using the same machine with the machine improperly configured.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
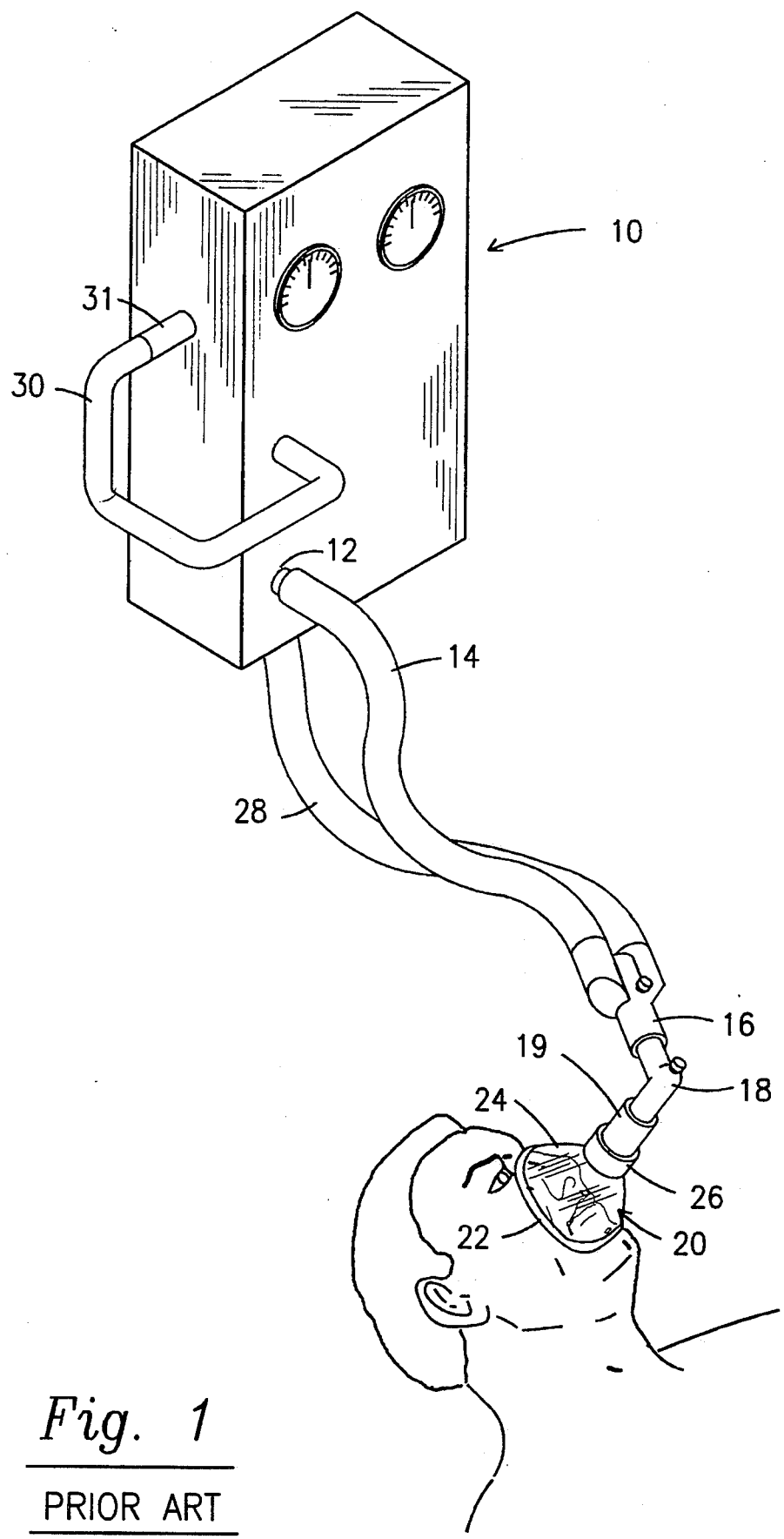
FIG. 1 is a perspective view of a prior art anesthesia machine configured to deliver a mixture of anesthesia and oxygen to a patient.

Turning now to FIG. 1, it will there be seen that an anesthesia machine of the prior art is depicted in diagrammatic form and is denoted 10 as a whole.

Outlet port 12 is in fluid communication with a source of anesthesia and oxygen and is adapted to receive the proximal end of elongate, flexible anesthesia supply tube 14. The distal end of tube 14 is in fluid communication with a housing 16 which includes an outlet conduit 18. Conduit 18 has a ninety degree bend formed therein as shown and coupler 19 attached to the distal end thereof is adapted to engage a facemask 20.

Facemask 20 has a soft peripheral rim 22 configured to fit around a patient's nose and mouth, and a converging sidewall 24 of frusto-conical configuration. Tubular facemask connector means 26 is fixedly secured to said sidewall at its smallest diameter and is adapted to releasably engage coupler 19. More particularly, coupler 19 has an external diameter slightly smaller than the internal diameter of connector means 26 and is therefore tightly press fit therewithin. Facemask 20 is employed in the well-known way to deliver anesthesia and oxygen to the patient, i.e., a mixture of nitrous oxide and oxygen from machine 10 flows through anesthesia tube 14 and conduit 18 to enter the interior of the facemask.

In the claims that follow, coupler 19 is referred to as the facemask coupler.

An elongate, flexible return tube 28 extends from housing 16 to the machine; it returns carbon dioxide and other exhaled gases. Note also oxygen hose 30 that is secured to oxygen outlet port 31; when machine 10 is configured as depicted in FIG. 1, it is fully operational.

It should be understood from the outset that a machine configured in the manner depicted in FIG. 1 can also deliver oxygen only to the patient, but only if the facemask is used. Thus, the FIG. 1 configuration cannot be used when use of a facemask would hinder the surgeon's freedom of movement or otherwise interfere with the operation. No facemask can be worn during an eye or nose operation, for example.

Figure 2:
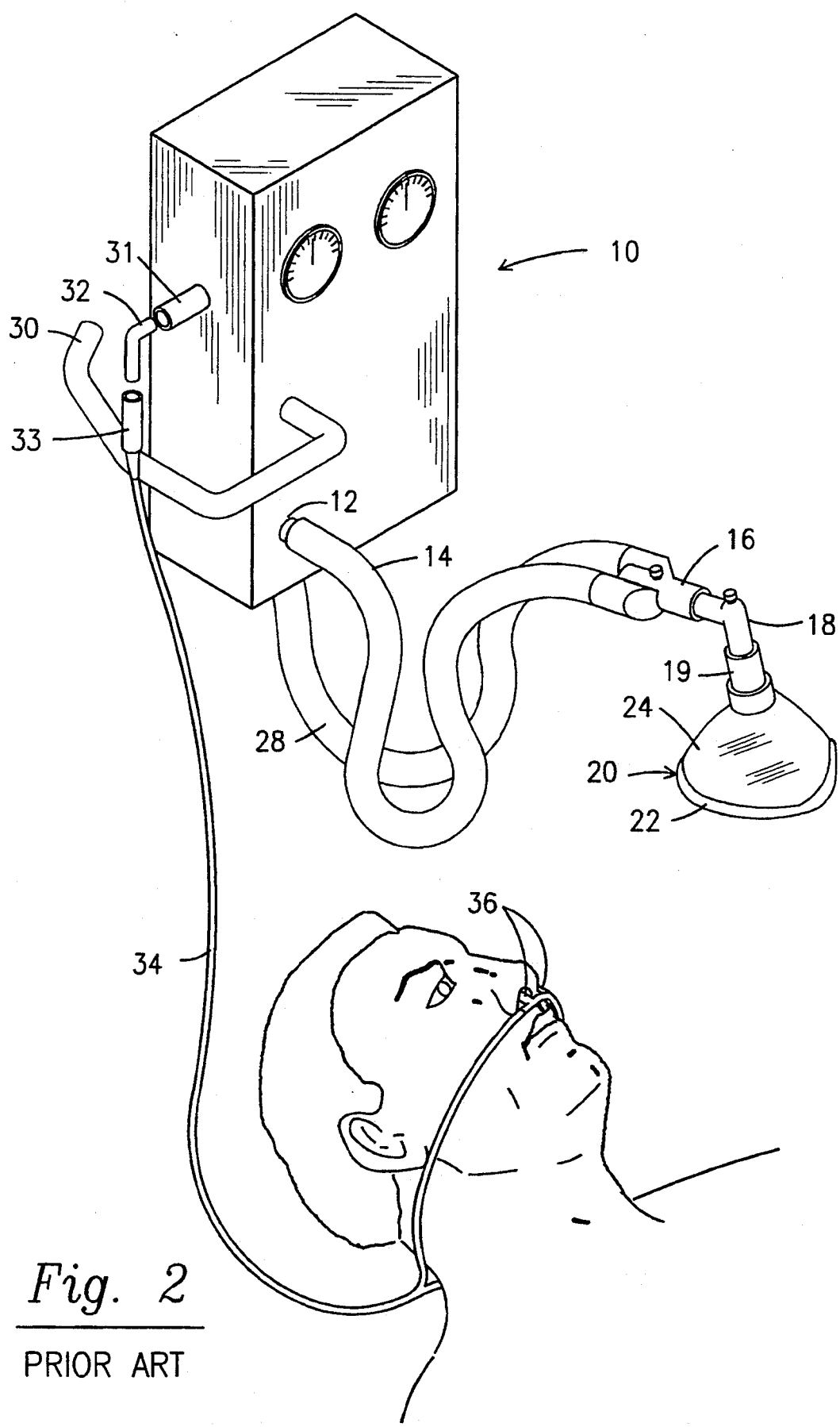
FIG. 2 is a perspective view of the machine of FIG. 1 configured to deliver oxygen only to the patient.

Thus, when machine 10 is used in accordance with the equipment and techniques of the prior art, when oxygen only is to be delivered during an eye, nose, lip, or other facial surgical procedure, an alternative route for the oxygen must be established. The alternative route is provided by an elbow member 32, shown in FIG. 2, which must be installed and used in connection with a nasal oxygen catheter. More particularly, conventional coupler 33 connected to the proximal end of elongate nasal oxygen catheter 34 is releasably attached to a first end of said elbow 32, and a second end of said elbow 32 is secured to oxygen outlet port 31 to which oxygen hose 30 is normally attached. Thus, whenever elbow 32 is in use, oxygen hose 30 is not, as should be clear from FIG. 2. A pair of nostril prongs, collectively denoted 36, are formed in said catheter 34 at the distal free end thereof. When a patient is receiving local anesthesia only, as depicted in FIG. 2, oxygen only is delivered to said patient through said catheter 34 and facemask 24 is not employed. It is important to note that this configuration of machine 10 disables its ability to deliver nitrous oxide to the patient because oxygen must flow through hose 30 in order to entrain nitrous oxide into tube 14. When the oxygen is re-routed through nasal oxygen catheter 34 by means of elbow 32, said nitrous oxide-delivering capability is disabled.

Should a patient receiving oxygen through catheter 34 require general anesthesia on an emergency basis, it is necessary to remove the nasal prongs at the distal end of the nasal oxygen catheter 34 from the patient's nostrils, detach elbow 32 from oxygen outlet port 31, reattach hose 30 onto said port 31, and apply the facemask. This configuration enables the delivery of a mixture of anesthesia and oxygen to the patient as desired, i.e., it is the FIG. 1 configuration. Again, about three minutes will elapse before the machine is returned to its FIG. 1 configuration.

Figure 3:
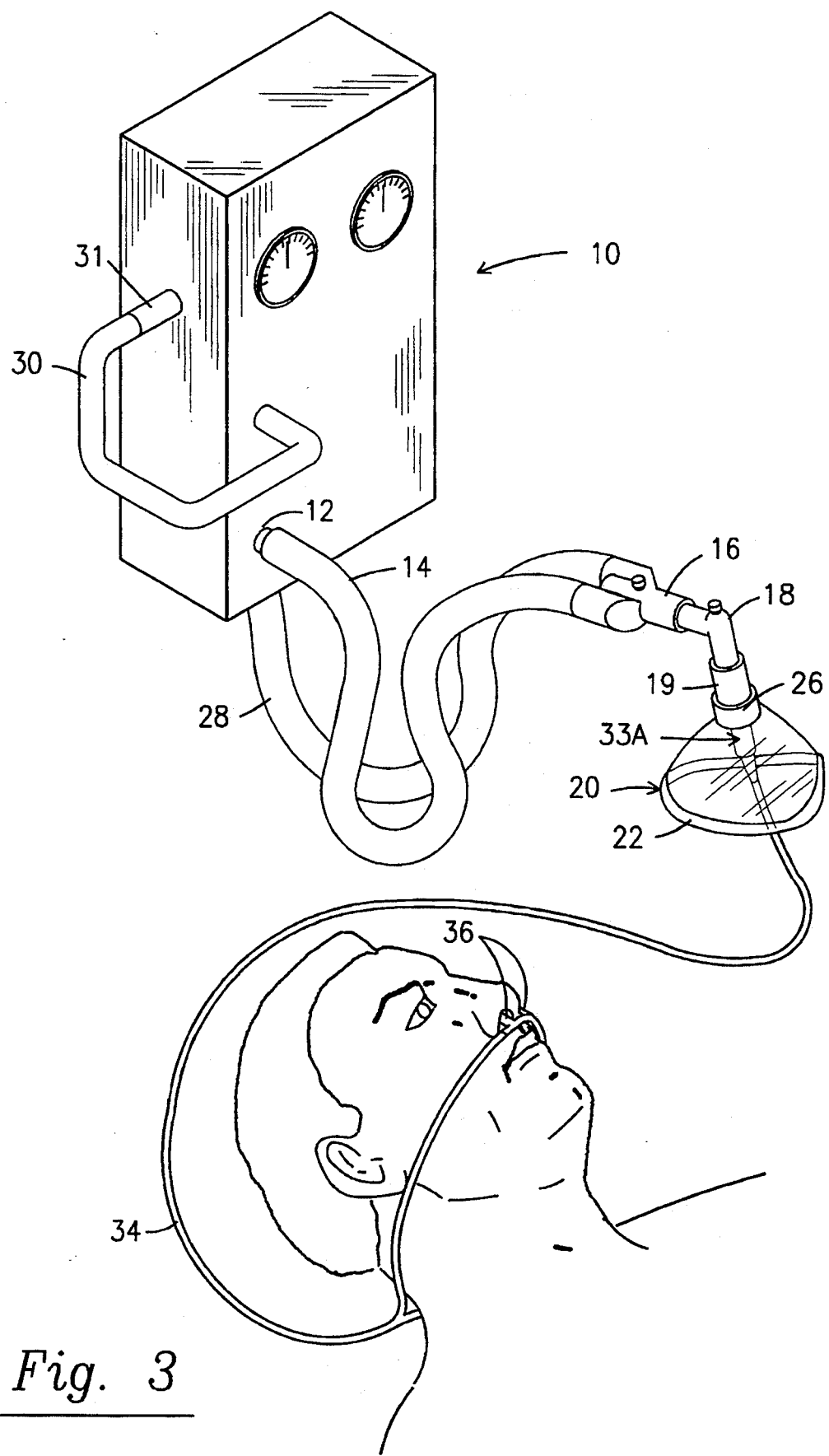
FIG. 3 is a perspective view of the novel anesthesia machine configured to deliver oxygen only to a patient receiving local anesthesia.
Figure 4:
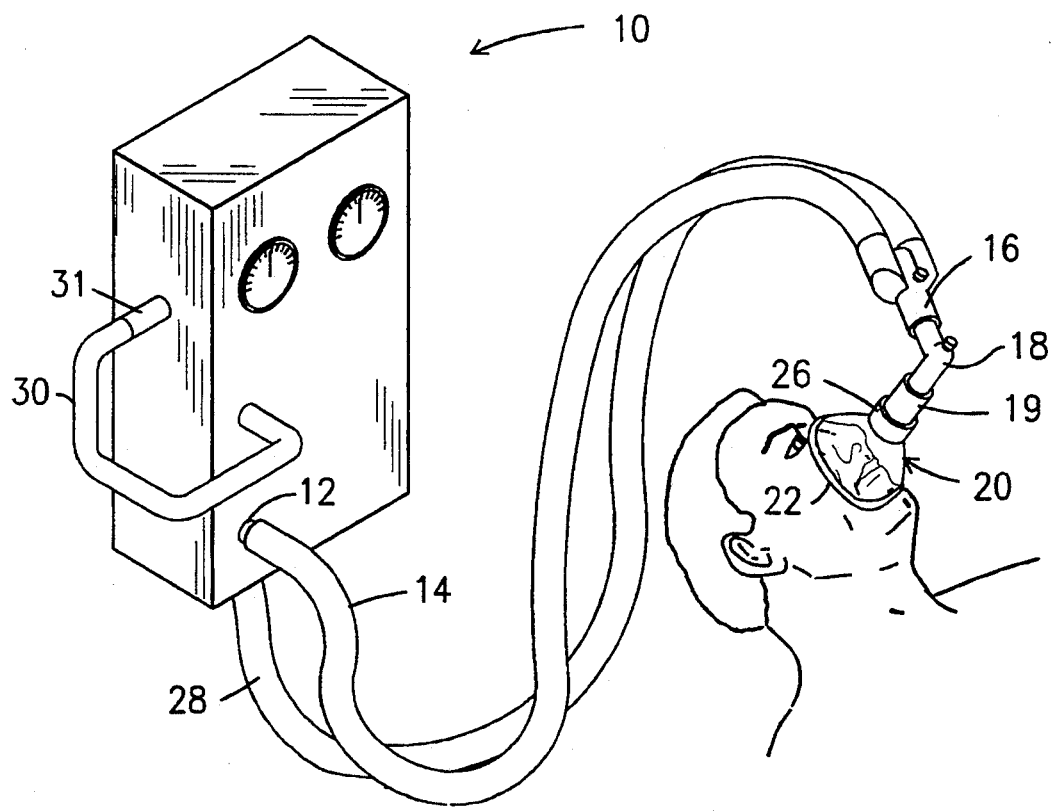
FIG. 4 is a perspective view of the novel machine configured to deliver anesthesia and oxygen to a patient.
Figure 5:
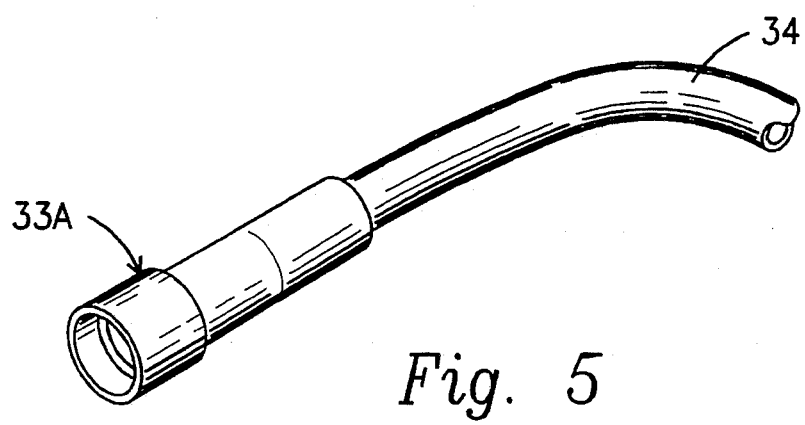
FIG. 5 is a perspective view of the proximal end of the novel nasal oxygen catheter.

The novel apparatus is depicted in FIGS. 3-5. In FIG. 3, the machine is configured to deliver oxygen only to a patient and in FIG. 4 it is configured to deliver anesthesia and oxygen. FIG. 5 shows the proximal end of the novel nasal oxygen catheter that makes possible the configuration of FIG. 3 and which facilitates the changeover from the configuration of FIG. 3 to the configuration of FIG. 4.

More particularly, a novel connector 33A is attached to the proximal end of catheter 34 and said connector 33A is specifically dimensioned and configured to releasably engage facemask coupler 19. More particularly, said connector 33A has an external diameter slightly less than the internal diameter of said facemask coupler 19 and is press fit therewithin. Thus, oxygen only or a mixture of anesthesia and oxygen may be delivered to conduit 18 and hence to catheter 34 when connector 33A is engaged to coupler 19.

The prior art counterpart of connector 33A is part 33 (FIG. 2) which is configured and dimensioned for releasable engagement with elbow member 32 as aforesaid, and said prior art counterpart is not attachable to facemask coupler 19 because it is too small in diameter, i.e., it was never intended to attach to any item other than elbow 32. Accordingly, it cannot be employed to enable the delivery of a mixture of nitrous oxide and oxygen to the nasal prongs at the distal end of the nasal oxygen catheter.

The advantages that flow from the insight that connector 33 at the proximal end of catheter 34 can be modified to produce connector 33A for connection to facemask coupler 19 are many. Most importantly, it eliminates any need to install elbow 32 when it is desired to deliver oxygen only to the patient. Thus, it avoids any configuration of the machine that disables its ability to deliver a nitrous oxide/oxygen mixture to the facemask. Moreover, if a need arises to place the patient under general anesthesia on an emergency basis, the anesthesiologist merely needs to remove the nasal prongs from the patient's nostrils, disconnect connector 33A of catheter 34 from the facemask coupler 19, and place the facemask 30 over the patient's nose and mouth. The machine is then set to deliver the desired mixture of nitrous oxide and oxygen; again, this procedure requires only a second or two, as should be clear upon observing the difference between FIGS. 3 and 4.

Upon conclusion of the surgical procedure, if the machine is left with the nasal oxygen catheter detached from facemask coupler 19, it is a simple matter for the next users of the machine to attach connector 33A to coupler 19 of conduit 18 if local anesthesia is to be used. If the machine is left with connector 33A engaged to coupler 19 (which should never happen since catheter 34 is discarded after each use), it is a simple matter to disengage said parts and the machine is ready for normal facemask-applied general anesthesia.

In summary, the only modification to catheter 34 is to enlarge conventional connector 33 so that it releasably engages facemask coupler 19 instead of elbow 32; this enables administration of oxygen only to the patient without disabling the ability of the machine to deliver anesthesia on a moment's notice.

Significantly, since the machine's ability to deliver anesthesia to the facemask 20 is never disabled, the anesthesiologist can deliver whatever amounts of anesthesia may be required to a patient who is receiving primarily oxygen only during a local anesthesia procedure, i.e., the facemask need not be employed where relatively small amounts of nitrous oxide are delivered to a patient receiving local anesthesia. Under the prior art system, no amount of nitrous oxide could be delivered to a patient when the machine was in its FIG. 2 configuration.

Moreover, it should be noted that connector 33A may be formed integrally with catheter 34, or it may be provided as a separate part which is press fit or otherwise secured to the proximal end of said catheter 34.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. An apparatus, for use with an anesthesia machine and a facemask, for selectively delivering anesthesia and oxygen to a patient, or oxygen only, comprising:
   an elongate nasal oxygen catheter having a connector at a proximal end thereof and a pair of nasal prongs at a distal end thereof;
   a facemask having a facemask coupler;
   said facemask coupler having a proximal end and a distal end;
   said proximal end of said facemask coupler being in fluid communication with an anesthesia machine;
   said distal end of said facemask coupler being releasably engageable by said connector of said elongate nasal oxygen catheter; and
   said connector specifically configured and dimensioned to releasably engage said facemask coupler;
   said elongate nasal catheter having a first configuration having said connector engaging said face mask coupler and communicating a mixture of anesthesia and oxygen or oxygen only between said facemask coupler and a patient's nostrils through said elongate nasal catheter without requiring disabling reconfiguration of the anesthesia machine;

said elongate nasal catheter having a second configuration disconnected from said facemask coupler and from said patient's nostrils, said facemask delivering a mixture of anesthesia and oxygen to a patient when said elongate nasal catheter is in said second configuration.

2. A method for delivering anesthesia, a mixture of anesthesia and oxygen, or oxygen to at patient, comprising the steps of:

providing an elongate nasal catheter having nasal prongs at a distal end thereof and a connector at a proximal end thereof;

providing a facemask having a peripheral rim for engaging a patients face, a sidewall of frustoconical configuration extending up from said peripheral rim to a small diameter opening, and a facemask coupler connected to said sidewall at said small diameter opening;

inserting said nasal prongs into the nostrils of a patient;

inserting said connector into said facemask coupler; and employing an anesthesia machine to supply anesthesia, a mixture of anesthesia and oxygen, or oxygen to said elongate nasal catheter.

* * * * *